United States Patent
Lin et al.

(10) Patent No.: US 7,118,695 B2
(45) Date of Patent: ***Oct. 10, 2006

(54) DUAL FUNCTION PROSTHETIC BONE IMPLANT AND METHOD FOR PREPARING THE SAME

(75) Inventors: Jiin-Huey Chern Lin, Winnetka, IL (US); Chien-Ping Ju, Carbondale, IL (US); Chih-Hung Tsai, Taichung (TW)

(73) Assignee: Calcitec, Inc., Austin, TX (US)

( * ) Notice: Subject to any disclaimer, the term of this patent is extended or adjusted under 35 U.S.C. 154(b) by 4 days.

This patent is subject to a terminal disclaimer.

(21) Appl. No.: 11/060,048

(22) Filed: Feb. 17, 2005

(65) Prior Publication Data

US 2005/0263922 A1 Dec. 1, 2005

Related U.S. Application Data

(63) Continuation of application No. 10/852,167, filed on May 25, 2004, now Pat. No. 6,994,726.

(51) Int. Cl.
*A61F 2/28* (2006.01)
*B29C 39/02* (2006.01)

(52) U.S. Cl. .................. 264/42; 264/49; 264/333
(58) Field of Classification Search ............... 264/42, 264/49, 333, 87, 250, 251, 86; 623/16.11, 623/17.11, 23.51, 23.62
See application file for complete search history.

(56) References Cited

U.S. PATENT DOCUMENTS

| | | |
|---|---|---|
| 3,679,360 A | 7/1972 | Rubin et al. |
| 4,371,484 A | 2/1983 | Inukai et al. |
| 4,481,175 A | 11/1984 | Iino et al. |
| 4,518,430 A | 5/1985 | Brown et al. |
| 4,553,272 A | 11/1985 | Mears |
| 4,612,053 A | 9/1986 | Brown et al. |
| 4,623,553 A | 11/1986 | Ries et al. |
| RE33,161 E * | 2/1990 | Brown et al. ............... 423/308 |
| RE33,221 E | 5/1990 | Brown et al. |
| 4,959,104 A | 9/1990 | Iino et al. |
| 5,017,518 A | 5/1991 | Hirayama et al. |
| 5,053,212 A | 10/1991 | Constantz et al. |
| 5,092,888 A | 3/1992 | Iwamoto et al. |
| 5,149,368 A | 9/1992 | Liu et al. |
| 5,152,791 A | 10/1992 | Hakamatsuka et al. |
| 5,164,187 A | 11/1992 | Constantz et al. |
| 5,180,426 A | 1/1993 | Sumita |
| 5,262,166 A | 11/1993 | Liu et al. |
| 5,336,264 A | 8/1994 | Constanz et al. |
| 5,338,356 A | 8/1994 | Hirano et al. |

(Continued)

FOREIGN PATENT DOCUMENTS

EP 0267624 5/1988

(Continued)

OTHER PUBLICATIONS

PCT/US04/11637 Inetrnational Search Report/Written Opinion, Oct. 2004, Examiner Koslow.

(Continued)

*Primary Examiner*—Mary Lynn Theisen
(74) *Attorney, Agent, or Firm*—Meyertons, Hood, Kivlin, Kowert & Goetzel, P.C.; Eric B. Meyertons

(57) ABSTRACT

The present invention discloses a prosthetic bone implant made of a hardened calcium phosphate cement having an apatitic phase as a major phase, which includes a dense cortical portion bearing the majority of load and a porous cancellous portion allowing a rapid blood/body fluid penetration and tissue ingrowth.

14 Claims, 3 Drawing Sheets

U.S. PATENT DOCUMENTS

| | | |
|---|---|---|
| 5,342,441 A | 8/1994 | Mandai et al. |
| 5,409,982 A | 4/1995 | Imura et al. |
| 5,476,647 A | 12/1995 | Chow et al. |
| 5,492,768 A | 2/1996 | Okimatsu et al. |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,605,713 A | 2/1997 | Boltong |
| 5,607,685 A | 3/1997 | Cimbollek et al. |
| 5,652,016 A | 7/1997 | Imura et al. |
| 5,683,461 A | 11/1997 | Lee et al. |
| 5,683,496 A | 11/1997 | Ison et al. |
| 5,695,729 A | 12/1997 | Chow et al. |
| 5,697,981 A | 12/1997 | Ison et al. |
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,018,095 A * | 1/2000 | Lerch et al. ............... 128/898 |
| 6,027,742 A | 2/2000 | Lee et al. |
| 6,077,989 A | 6/2000 | Kandel et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,149,688 A | 11/2000 | Brosnahan et al. |
| 6,162,258 A | 12/2000 | Scarborough et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,323,146 B1 | 11/2001 | Pugh et al. |
| 6,325,987 B1 | 12/2001 | Sapieszko et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 | 4/2002 | Lin et al. |
| 6,440,444 B1 | 8/2002 | Boyce et al. |
| 6,458,162 B1 | 10/2002 | Koblish et al. |
| 6,478,825 B1 | 11/2002 | Winterbottom et al. |
| 6,495,156 B1 | 12/2002 | Wenz et al. |
| 6,530,955 B1 | 3/2003 | Boyle et al. |
| 6,547,866 B1 | 4/2003 | Edwards et al. |
| 6,569,489 B1 | 5/2003 | Li |
| 6,585,992 B1 | 7/2003 | Pugh et al. |
| 6,616,742 B1 | 9/2003 | Lin et al. |
| 6,648,960 B1 | 11/2003 | Lin et al. |
| 6,670,293 B1 | 12/2003 | Edwards et al. |
| 6,696,073 B1 | 2/2004 | Boyce et al. |
| 6,719,989 B1 | 4/2004 | Matsushima et al. |
| 6,752,831 B1 | 6/2004 | Sybert et al. |
| 6,793,725 B1 | 9/2004 | Chow et al. |
| 6,808,561 B1 | 10/2004 | Genge et al. |
| 6,808,585 B1 | 10/2004 | Boyce et al. |
| 6,840,995 B1 | 1/2005 | Lin et al. |
| 6,929,692 B1 | 8/2005 | Tas |
| 6,953,594 B1 | 10/2005 | Lee et al. |
| 6,955,716 B1 | 10/2005 | Xu et al. |
| 6,960,249 B1 | 11/2005 | Lin et al. |
| 2002/0019635 A1 | 2/2002 | Wenstrom, Jr. et al. |
| 2002/0073894 A1 | 6/2002 | Genge et al. |
| 2002/0137812 A1 | 9/2002 | Chow et al. |
| 2002/0169066 A1 | 11/2002 | Cassidy et al. |
| 2003/0019396 A1 | 1/2003 | Edwards et al. |
| 2003/0021824 A1 * | 1/2003 | Lacout et al. ............... 424/423 |
| 2003/0031698 A1 | 2/2003 | Roeder et al. |
| 2003/0039676 A1 | 2/2003 | Boyce et al. |
| 2003/0055512 A1 | 3/2003 | Genin et al. |
| 2003/0074081 A1 | 4/2003 | Ayers et al. |
| 2003/0078317 A1 | 4/2003 | Lin et al. |
| 2003/0120351 A1 | 6/2003 | Tofighi |
| 2003/0121450 A1 | 7/2003 | Lin et al. |
| 2003/0167093 A1 | 9/2003 | Xu et al. |
| 2003/0216777 A1 | 11/2003 | Tien et al. |
| 2004/0003757 A1 | 1/2004 | Chern Lin et al. |
| 2004/0022825 A1 | 2/2004 | Lagow |
| 2004/0031420 A1 | 2/2004 | Lin et al. |
| 2004/0076685 A1 | 4/2004 | Tas |
| 2004/0137032 A1 | 7/2004 | Wang |
| 2004/0175320 A1 | 9/2004 | Lin et al. |
| 2004/0180091 A1 | 9/2004 | Lin |
| 2004/0185181 A1 | 9/2004 | Matsumoto |
| 2004/0186481 A1 | 9/2004 | Chern Lin et al. |
| 2005/0008759 A1 | 1/2005 | Nie et al. |
| 2005/0076813 A1 | 4/2005 | Lin et al. |
| 2005/0101964 A1 | 5/2005 | Lin et al. |
| 2005/0184417 A1 | 8/2005 | Chern Lin et al. |
| 2005/0186354 A1 | 8/2005 | Lin et al. |
| 2005/0263919 A1 | 12/2005 | Lin et al. |
| 2005/0263920 A1 | 12/2005 | Lin et al. |
| 2005/0263922 A1 | 12/2005 | Lin et al. |
| 2005/0263927 A1 | 12/2005 | Lin et al. |
| 2005/0263928 A1 | 12/2005 | Lin et al. |
| 2005/0263929 A1 | 12/2005 | Lin et al. |
| 2005/0263930 A1 | 12/2005 | Lin et al. |
| 2005/0263931 A1 | 12/2005 | Lin et al. |
| 2005/0267587 A1 | 12/2005 | Lin et al. |
| 2005/0267588 A1 | 12/2005 | Lin et al. |
| 2005/0267589 A1 | 12/2005 | Lin et al. |
| 2005/0267592 A1 | 12/2005 | Lin et al. |
| 2005/0267593 A1 | 12/2005 | Lin et al. |
| 2005/0267604 A1 | 12/2005 | Lin et al. |

FOREIGN PATENT DOCUMENTS

| | | |
|---|---|---|
| JP | 06-228011 | 8/1994 |
| WO | WO 03/055418 | 7/2003 |

OTHER PUBLICATIONS

PCT/US04/11637 International Search Report/Written Opinion, mailed Mar. 11, 2005, Examiner Boehm.

Sugawara et al., "Calcium Phosphate Cement: An In Vitro Study of Dentin Hypersensitivity Using Calcium Phosphate Cement", The Journal of the Japanese Society for Dental Materials and Devices, 1989, vol. 8, pp. 282-294.

Pickel et al., "The Effects of a Chewing Gum Containing Dicalcium Phosphate on Salivary Calcium and Phosphate", Ala. J. Med. Sci., 1965, vol. 2, pp. 286-287.

Matsuya et al., "Effects of pH on the Reactions of Tetracalcium Phosphate and Dicalcium Phosphate", IADR Abstact, Apr. 1991.

Sugawara et al., "Formation of Hydroxyapatite in Hydrogels from Tetracalcium Phosphate/Dicalcium Phosphate Mixtures," J. Nihon. Univ. Sch. Dent., 1989, vol. 31, pp. 372-381.

Hong et al., "The Periapical Tissue Reactions to a Calcium Phosphate Cement in the Teeth of Monkeys," J. Biomed. Mater. Res., Apr. 1991, vol. 25(4), pp. 485-498.

de Rijk, et al., "Clinical Evaluation of a Hydroxyapatite Precipitate for the Treatment of Dentinal Hypersensitivity," Biomedical Engineering v. Recent Developments, Proc. of 5th Southern Biomedical Engineering Conference, 1986, pp. 336-339. (Pergamon Press, New York).

Gruninger et al., "Evaluation of the Biocompatability of a New Calcium Phosphate Setting Cement," J. Dent. Res., 1984, 63, Abst. No. 270 (4 pages).

Costantino et al., "Evaluation of a New Hydroxyapatite Cement: Part III: Cranioplasty in a Cat Model," The Fifth Intl. Symposium on Facial Plastic Reconstructive Surgery of the Head and Neck, Toronto, Canada, 1989. (18 pages).

Shindo, et al., "Facial Skeletal Augmentation Using Hydroxyapatite Cement," Arch. Otolaryngol. Head Neck Surg., 1993, vol. 119, pp. 185-190.

Briner et al., "Significance of Enamel Remineralization", J. Dent. Res., 1974, vol. 53, pp. 239-243.

Silverstone L.M., "Remineralization Phenomena", Caries Res., 1977, vol. 11 (Supp. 1), pp. 59-84.

Costantino et al., "Hydroxyapatite Cement: I. Basic Chemistry and Histologic Properties," Arch. Otolaryngol. Head Neck Surg., 1991, vol. 117, pp. 379-394.

Friedman et al., "Hydroxyapatite Cement: II. Obliteration and Reconstruction of the Cat Frontal Sinus," Arch. Otolary. Head Neck Surg., 1991, vol. 117, pp. 385-389.

Costantino et al., "Experimental Hydroxyapatite Cement Cranioplasty," Plast. Reconstr. Surg., 1992, vol. 90, No. 2, pp. 174-185.

Miyazaki et al., "An Infrared Spectroscopic Study of Cement Formation of Polymeric Calcium Phosphate Cement," The Journal of the Japanese Society for Dental Materials and Devices, 1992, vol. 11, No. 2, pp. 278-284.

Driskell et al., "Development of Ceramic and Ceramic Composite Devices for Maxillofacial Applications", J. Biomed. Mater. Res. Symposium, 1972, vol. 6, No. 2 (part 2), pp. 345-361.

Hiatt et al., "Root Preparation I. Obturation of Dentinal Tubules in Treatment of Root Hypersensitivity", J. Periodontol., 1972, vol. 41, No. 6, pp. 373-380.

Patel et al., "Solubility of $CaHPO_4$ $2H_2O$ in the Quaternary System $Ca(OH)_2$-$H_3PO_4$-NaCl-$H_2O$ at 25° C.," J. Res. Nat. Bur. Stand. (Physics Chem.), 1974, vol. 78A, pp. 675-681.

Salyer et al., "Porous Hydroxyapatite as on Onlay Bone-Graft Substitute for Maxillofacial Surgery," Presented at the 54th Annual Scientific Meeting of the American Society of Plastic and Reconstructive Surgeons, Kansas City, Missouri, 1985, pp. 236-244.

Kenney et al., "The Use of a Porous Hydroxylapatite Implant in Periodontal Defects: II. Treatment of Class II Furcation Lesions in Lower Molars," J. Periodontol, 1988, pp. 67-72.

Zide et al., "Hydroxylapatite Cranioplasty Directly Over Dura," J. Oral Maxillofac. Surg., 1987, vol. 45, pp. 481-486.

Waite et al., "Zygomatic Augmentation with Hydroxylapatite: A Preliminary Report," J. Oral Maxillofac. Surg., 1986, pp. 349-352.

Verwoerd, et al. Porous Hydroxylapatite-perichondrium Graft in Cricoid Reconstruction, Acta Otolaryngol., 1987, vol. 103, pp. 496-502.

Grote, "Tympanoplasty With Calcium Phosphate," Arch. Otolaryngol., 1984, vol. 110, pp. 197-199.

Kent et al., "Alveolar Ridge Augmentation Using Nonresorbable Hydroxylapatite with or without Autogenous Cancellous Bone," J. Oral Maxillofac. Surg., 1983, vol. 41, pp. 629-642.

Piecuch, J.F., "Augmentation of the Atrophic Edentulous Ridge with Porous Replamineform Hydroxyapatite (Interpore-200)", Dental Clinics of North America, 1986, vol. 30(2), pp. 291-305.

Misch, C.E., "Maxillary Sinus Augmentation for Endosteal Implants: Organized Alternative Treatment Plans," Int. J. Oral. Implant., 1987, vol. 4(2), pp. 49-58.

Chohayeb, et al., "Evaluation of Calcium Phosphate as a Root Canal Sealer-Filler Material," J. Endod., 1987, vol. 13, pp. 384-386.

Brown et al., "Crystallography of Tetracalcium Phosphate," J. Res. Nat. Bur. Stand. (Physics Chem.), 1965, vol. 69A, pp. 547-551.

Sanin et al., "Particle Size Effects on pH and Strength of Calcium Phosphate Cement," IADR Abstract, Apr. 1991.

Chow et al., "X-ray Diffraction and Electron Microscopic Characterization of Calcium Phosphate Cement Setting Reactions," IADR Abstract, 1987.

Block et al. "Correction of Vertical Orbital Dystopia with a Hydroxylapatite Orbital Floor Graft," J. Oral Maxillofac. Surg., 1988, vol. 46, pp. 420-425.

Brown, W.E., "Solubilities of Phosphates and Other Sparingly Soluble Compounds", Environmental Phosphorous Handbook, 1973, pp. 203-239. (John Wiley & Sons, New York).

Gregory et al., "Solubility of $CaHPO_4$ $2H_2O$ in the System $Ca(OH)_2$-$H_3PO_4$-$H_2O$ at 5, 15, 25, and 37.5° C.," J. Res. Nat. Bur. Stand. (Physics Chem.), 1970, vol. 74A, No. 4, pp. 461-475.

Gregory et al., "Solubility of $\beta$-$Ca_3(PO_4)_2$ in the System $Ca(OH)_2$-$H_3PO_4$-$H_2O$ at 5, 15, 25, and 37° C.," J. Res. Nat. Bur. Stand. (Physics Chem.), 1974, vol. 78A, No. 6, pp. 667-674.

McDowell et al., "Solubility of $Ca_5(PO_4)_3OH$ in the System $Ca(OH)_2$-$H_3PO_4$-$H_2O$ at 5, 15, 25 and 37° C.," J. Res. Nat. Bur. Stand. (Physics Chem.), 1977, vol. 91A, Nos. 2 and 3, pp. 273-281.

McDowell et al., "Solubility Study of Calcium Hydrogen Phosphate. Ion Pair Formation," Inorg. Chem., 1971, vol. 10, pp. 1638-1643.

Moreno et al., "Stability of Dicalcium Phosphate Dihydrate in Aqueous Solutions and Solubility of Octocalcium Phosphate," Proc. Soil Sci. Soc. Am., 1960, vol. 21, pp. 99-102.

Chow et al, "Self-Setting Calcium Phosphate Cements," Mat. Res. Soc. Symp. Proc., vol. 179, 1991, pp. 3-23.

Miyazaki et al., "Chemical Change of Hardened PCA/CPC Cements in Various Storing Solutions", The Journal of the Japanese Society for Dental Materials and Devices, 1992, vol. 11, No. 2, pp. 324-330.

Fukase et al, "Thermal Conductivity of Calcium Phosphate Cement", IADR Abstract, Mar. 1990.

Sugawara et al., "Biocompatibility and Osteoconductivity of Calcium Phosphate Cement", IADR Abstract, Mar. 1990.

Miyazaki et al., "Polymeric Calcium Phosphate Cements", IADR Abstract, Mar. 1990.

Link et al., "Composite of Calcium Phosphate Cement and Genetically Engineered Protein Bioadhesive," IADR Abstract, Mar. 1991.

Matsuya et al., "Effects of pH on the Reactions of Tetracalcium Phosphate and Dicalcium Phosphate", IADR Abstract, Apr. 1991.

Briner et al., "Significance of Enamel Remineralization", J. Dent. Res., 1974, vol. 53, pp. 239-243.

Chow, "Development of Self-Setting Calcium Phosphate Cements", Journal of The Ceramic Society of Japan, 1991, vol. 99 [10], pp. 954-964.

Brown et al., A New Calcium Phosphate, Water Setting Cement, Cements Research Progress 1986, P.W. Brown, Ed., Westerville, Ohio: American Ceramic Society, 1988, pp. 352-379.

Sugawara et al., "A Calcium Phosphate Root Canal Sealer-Filler" IADR Abstract, 1987.

Sugawara et al., "In Vitro Evaluation of the Sealing Ability of a Calcium Phosphate Cement When Used as a Root Canal Sealer-Filler," J. Endodon., 1990, vol. 16, No. 4, pp. 162-165.

Chow, L.C., "Calcium Phosphate Materials: Reactor Response," Adv. Dent. Res., 1988, vol. 2(1), pp. 181-184.

Fukase et al., "Setting Reactions and Compressive Strengths of Calcium Phosphate Cements", J. Dent. Res., 1990, vol. 69(12), pp. 1852-1856.

Miyazaki et al., "Cements," Guide to Dental Materials and Devices, 7th Edition, 1974-1975, Chapter 6.

Sugawara et al., "Formation of Hydroxyapatite in Hydrogels from Tetracalcium Phosphate/Dicalcium Phosphate Mixtures," J. Nihon Univ. Sch. Dent., vol. 31, 372-381, 1989.

Chow et al., "A Natural Bone Cement-A Laboratory Novelty Led to the Development of Revolutionary New Biomaterials", J. Res. Natl. Inst. Stand. Technol., 2001, vol. 106, pp. 1029-1033.

Gburek et al., "Mechanical Activation of Tetracalcium Phosphate," J. Am. Ceramics Soc., vol. 87(2), pp. 311-313.

* cited by examiner

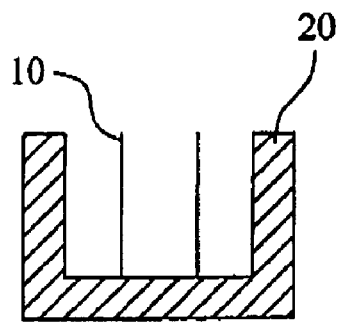
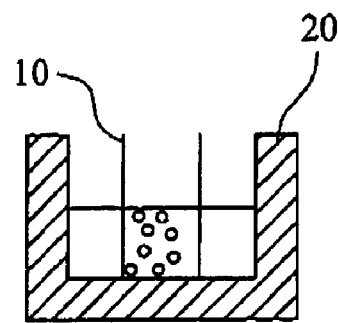
FIG. 2aFIG. 2b
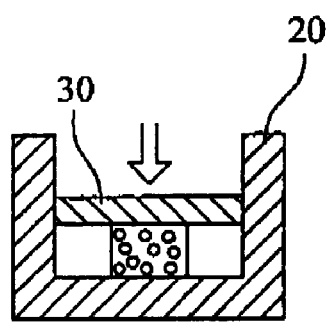
FIG. 2cFIG. 2d
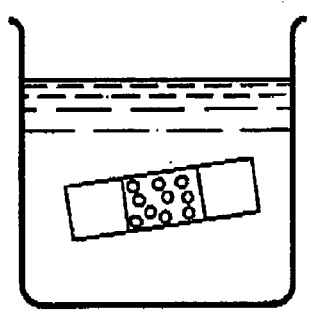
FIG. 2eFIG. 2f

DUAL FUNCTION PROSTHETIC BONE IMPLANT AND METHOD FOR PREPARING THE SAME

PRIORITY CLAIM

This application is a continuation of and claims priority to Non-Provisional patent application Ser. No. 10/852,167 entitled "DUAL FUNCTION PROSTHETIC BONE IMPLANT AND METHOD FOR PREPARING THE SAME" filed on May 25, 2004 now U.S. Pat. No. 6,994,726.

BACKGROUND OF THE INVENTION

1. Field of the Invention

The present invention is related to a prosthetic bone implant made of a hardened calcium phosphate cement having an apatitic phase as a major phase, and in particular to a prosthetic bone implant comprising a dense cortical portion bearing the majority of load and a porous cancellous portion allowing a rapid blood/body fluid penetration and tissue ingrowth.

2. Description of the Related Art

It is advantageous if a prosthetic bone implant is bioresorbable and is supportive at the same time. Accordingly, an article made of calcium phosphate will be preferable than that made of a metal, if the former has strength which is comparable to a human cortical bone. One way of making such a bone implant is by sintering a calcium phosphate powder, particularly a hydroxyapatite (HA) powder, into a block material at a temperature generally greater than 1000° C. Despite the fact that the high temperature-sintered HA block material has an enhanced strength, the bioresorbability of the material is largely sacrificed, if not totally destroyed, due to the elimination of the micro- and nano-sized porosity during the sintering process.

The conventional spinal fusing device is composed of a metallic cage and a bioresorbable material disposed in the metal cage, for example the one disclosed in U.S. Pat. No. 5,645,598. An inevitable disadvantage of this fusion device is the sinking of the metallic cage sitting between two vertebrae to replace or repair a defect spinal disk, because the hardness and the relatively small size of the cage wear out or break the bone tissue, and in particular the endplate of the vertebra.

SUMMARY OF THE INVENTION

A primary objective of the invention is to provide a prosthetic bone implant free of the drawbacks of the prior art.

The prosthetic bone implant constructed according to the present invention is made of a hardened calcium phosphate cement having an apatitic phase as a major phase, which comprises a dense cortical portion bearing the majority of load and a porous cancellous portion allowing a rapid blood/body fluid penetration and tissue ingrowth.

The prosthetic bone implant of the present invention is made by a novel technique, which involves immersing an article molded from two different pastes of calcium phosphate cement (CPC), one of them having an additional pore-forming powder, in a liquid for a period of time, so that the compressive strength of the molded CPC article is significantly improved after removing from the liquid while the pore-forming powder is dissolved in the liquid, creating pores in a desired zone or zones of the molded article.

Features and advantages of the present invention are as follows:

1. Easy process for different shape and size of the prosthetic bone implant of the present invention, so that the outer circumferential dense portion thereof can sit over the circumferential cortical portion of a bone and the porous portion thereof can contact the cancellous portion of the bone adjacent to a bone receiving treatment.
2. The dense cortical portion of the prosthetic bone implant made according to the present invention exhibits a high strength comparable to that of human cortical bone (about 110–170 MPa). The strength is adjustable by adjusting process parameters.
3. The dense cortical portion of the prosthetic bone implant made according to the present invention contains significant amount of micro- and nano-sized porosity, that improves bioresorbability thereof. Conventional high temperature-sintered HA block, on the other hand, does not possess sufficient micro/nano-sized porosity and is not bioresorbable.
4. The porous cancellous portion of the prosthetic bone implant made according to the present invention possesses a porosity greater than 40% in volume, preferably 40–90%, allowing rapid blood/body fluid penetration and tissue ingrowth, thereby anchoring the prosthetic bone implant.
5. A wide range of medical application includes bone dowel, spacer, cavity filler, artificial disc and fixation devices for spine and other locations, to name a few.

BRIEF DESCRIPTION OF THE DRAWINGS

FIGS. 2a to 2f are schematic cross sectional views showing steps of a method for preparing a prosthetic bone implant according to one embodiment of the present invention.

DETAILED DESCRIPTION OF THE INVENTION

Figure 1A:
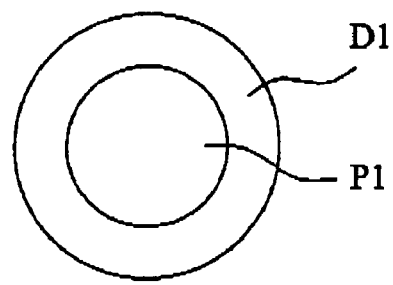
FIGS. 1a to 1d show schematic cross sectional views of four different designs of prosthetic bone implants constructed according to the present invention.

Preferred embodiments of the present invention includes (but not limited to) the following:

1. A prosthetic bone implant comprising a cortical portion having two opposite sides, and a cancellous portion integrally disposed in said cortical portion and being exposed through said two opposite sides, wherein said cortical portion comprises a hardened calcium phosphate cement has a porosity of less than 40% in volume, and said cancellous portion comprises a porous hardened calcium phosphate cement having a porosity greater than 20% in volume, and greater than that of said cortical portion.
2. The implant according to Item 1, wherein the cortical portion is in the form of a hollow disk, and the cancellous portion is in the form of a column surrounded by the hollow disk.
3. The implant according to Item 2 further comprising a transitional portion between said column and said hollow disk surrounding said central cylinder, which has properties range from those of said cancellous portion to said cortical portion.

4. The implant according to Item 1, wherein the cortical portion is in the form of a disk having one or more longitudinal through holes, and the cancellous portion is in the form of one or more columns surrounded by said one or more longitudinal through holes.
5. The implant according to Item 1, wherein said hardened calcium phosphate cement of said cortical portion comprises an apatitic phase as a major phase giving rise to broadened characteristic X-ray diffraction peaks in comparison with a high-temperature sintered apatitic phase.
6. The implant according to Item 5, wherein said broadened characteristic the X-ray diffraction peaks are at 2-Theta values of 25–27° and 30–35°.
7. The implant according to Item 1, wherein said hardened calcium phosphate cement of said cortical portion is prepared without a high temperature sintering.
8. The implant according to Item 1, wherein said hardened calcium phosphate cement of said cortical portion comprises an apatitic phase as a major phase having a Ca/P molar ratio of 1.5–2.0.
9. The implant according to Item 1, wherein said hardened calcium phosphate cement of said cancellous portion comprises an apatitic phase as a major phase giving rise to broadened characteristic X-ray diffraction peaks in comparison with a high-temperature sintered apatitic phase.
10. The implant according to Item 9, wherein said broadened characteristic the X-ray diffraction peaks are at 2-Theta values of 25–27° and 30–35°.
11. The implant according to Item 1, wherein said hardened calcium phosphate cement of said cancellous portion is prepared without a high temperature sintering.
12. The implant according to Item 1, wherein said hardened calcium phosphate cement of said cancellous portion comprises an apatitic phase as a major phase having a Ca/P molar ratio of 1.5–2.0.
13. The implant according to Item 1, wherein said cortical portion comprises 10–90% in volume of said implant.
14. The implant according to Item 1, wherein said cortical portion has a porosity of less than 30% in volume.
15. The implant according to Item 1, wherein said cancellous portion has a porosity greater than 40–90% in volume.
16. A method for preparing a prosthetic bone implant comprising a cortical portion having two opposite sides, and a cancellous portion integrally disposed in said cortical portion and being exposed through said two opposite sides, said method comprises the following steps:
  a) preparing a first paste comprising a first calcium phosphate cement and a first setting liquid;
  b) preparing a second paste comprising a second calcium phosphate cement, a pore-forming powder and a second setting liquid;
  c) i) preparing a shaped article in a mold having two or more cells separated by one more partition walls comprising introducing said first paste and said second paste into said two or more cells separately, and removing said one or more partition walls from said mold, so that said second paste in the form of a single column or two or more isolated columns is integrally disposed in the first paste in said mold; or ii) preparing a shaped article comprising introducing one of said first paste and said second paste into a first mold to form an intermediate in said first mold, placing said intermediate into a second mold after a hardening reaction thereof undergoes at least partially, and introducing another one of said first paste ad said second paste into said second mold, so that said second paste as a single column or as two or more isolated columns is integrally disposed in the first paste in said second mold;
  d) immersing the resulting shaped article from step c) in an immersing liquid for a first period of time so that said pore-forming powder is dissolved in the immersing liquid, creating pores in said single column or said two or more isolated columns; and
  e) removing the immersed shaped article from said immersing liquid.
17. The method according to Item 16 further comprising
  f) drying the immersed shaped article.
18. The method according to Item 16, wherein said pore-forming powder is selected from the group consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, and sodium lactate.
19. The method according to Item 16, wherein said first calcium phosphate cement comprises at least one Ca source and at least one P source, or at least one calcium phosphate source; and said second calcium phosphate cement comprises at least one Ca source and at least one P source, or at least one calcium phosphate source.
20. The method according to Item 19, wherein said first calcium phosphate cement comprises at least one calcium phosphate source, and said second calcium phosphate cement comprises at least one calcium phosphate source.
21. The method according to Item 20, wherein said calcium phosphate source is selected from the group consisting of alpha-tricalcium phosphate (α-TCP), beta-tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.
22. The method according to Item 21, wherein said first calcium phosphate cement and said second calcium phosphate cement are identical.
23. The method according to Item 22, wherein said first calcium phosphate cement and said second calcium phosphate cement are tetracalcium phosphate.
24. The method according to Item 16, wherein the first setting liquid and the second setting liquid independently are an acidic solution, a basic solution, or a substantially pure water.
25. The method according to Item 24, wherein said acidic solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate ($NaH_2PO_4 \cdot H_2O$), sodium dihydrogen phosphate dihydrate, sodium dihydrogen phosphate dehydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid and their mixture.

26. The method according to Item 22, wherein said basic solution is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4 \cdot 12H_2O$), dipotassium hydrogen phosphate ($K_2HPO_4$), potassium hydrogen phosphate trihydrate ($K_2HPO_4 \cdot 3H_2O$), potassium phosphate tribasic ($K_3PO_4$), diammonium hydrogen phosphate (($NH_4$)$_2HPO_4$), ammonium phosphate trihydrate (($NH_4$)$_3PO_4 \cdot 3H_2O$), sodium hydrogen carbonate ($NaHCO_3$), sodium carbonate $Na_2CO_3$, and their mixture.

27. The method according to Item 16, wherein step c-i) further comprises allowing said first paste and said second paste undergoing a hardening reaction in said mold.

28. The method according to Item 16, wherein step c-i) further comprises pressurizing said first paste and said second paste in said mold after removing said one or more partition walls from said mold to remove a portion of liquid from said first paste and said second paste, so that a liquid/powder ratio of said first paste and of said second paste decreases; and allowing said first paste and second paste undergoing a hardening reaction in said mold.

29. The method according to Item 16, wherein step c-ii) further comprises allowing said intermediate undergoing a hardening reaction in said first mold, and allowing said another one of said first paste and said second paste undergoing a hardening reaction in said second mold.

30. The method according to Item 16, wherein step c-ii) further comprises pressurizing said one of said first paste and said second paste in said first mold to remove a portion of liquid therefrom before the hardening reaction of said intermediate is completed; allowing said intermediate undergoing a hardening reaction in said first mold; pressuring said another one of said first paste and said second paste in said second mold, so that a liquid/powder ratio of said another one of said first paste and of said second paste decreases; and allowing said another one of said first paste and second paste undergoing a hardening reaction in said second mold.

31. The method according to Item 28, wherein said pressuring is about 1 to 500 MPa.

32. The method according to Item 30, wherein said pressuring is about 1 to 500 MPa.

33. The method according to Item 16, wherein the immersing liquid is an acidic aqueous solution, a basic aqueous solution, a physiological solution, an organic solvent, or a substantially pure water.

34. The method according to Item 33, wherein the immersing liquid comprises at least one of Ca and P sources.

35. The method according to Item 33, wherein the immersing liquid is a Hanks' solution, a HCl aqueous solution or an aqueous solution of ($NH_4$)$_2HPO_4$.

36. The method according to Item 16, wherein the immersing in step d) is carried out for a period longer than 10 minutes.

37. The method according to Item 16, wherein the immersing in step d) is carried out for a period longer than 1 day.

38. The method according to Item 16, wherein the immersing in step d) is carried out at a temperature of about 10 and 90° C.

39. The method according to Item 38, wherein the immersing in step d) is carried out at room temperature.

40. The method according Item 17 further comprising cleaning said immersed shaped article before said drying; and heating the resulting dried shaped article at a temperature between 50 and 500° C.

Figure 1B:
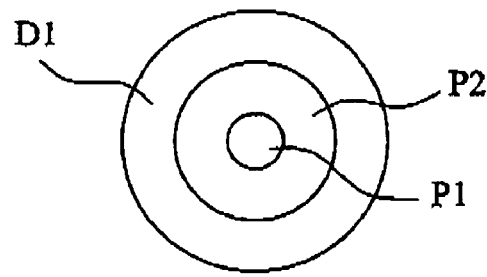
Figure 1C:
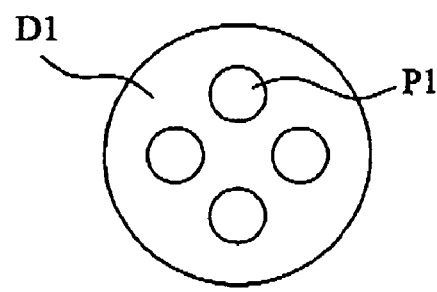
Figure 1D:
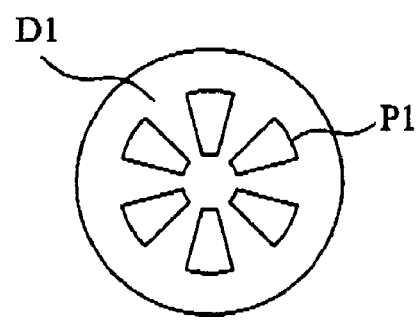

Four different designs of prosthetic bone implants constructed according to the present invention are shown in FIGS. 1a to 1d. In FIG. 1a, the prosthetic bone implant of the present invention has a dense cortical portion D1 in the tubular form and a porous cancellous portion P1 formed in the central through hole of the tubular cortical portion D1. Both the dense cortical portion D1 and the porous cancellous portion P1 are made of a hardened calcium phosphate cement having an apatitic phase as a major phase. In FIG. 1b, the prosthetic bone implant of the present invention has a dense cortical portion D1 in the tubular form; a cylindrical porous cancellous portion P1 in the center of the tubular cortical portion D1; and an annular transitional portion P2 connecting the tubular cortical portion D1 and the cylindrical cancellous portion P1. The transitional portion P2 is made of a hardened calcium phosphate cement having an apatitic phase as a major phase, and a porosity gradient increasing from the lower porosity of the cylindrical cancellous portion P1 to the higher porosity of the tubular cortical portion D1, which may be formed in-situ during molding of two different two different CPC pastes, one of them having an additional pore-forming powder for forming the cylindrical cancellous portion P1, and another one being a regular CPC powder for forming the dense cortical portion D1. The porous cancellous portion P1 may be in the forms of isolated columns surrounded by the dense cortical portion D1 as shown in FIGS. 1c and 1d. Other designs are also possible in addition to those shown in FIGS. 1a to 1d.

A suitable method for preparing the prosthetic bone implant of the present invention includes placing a tubular partition wall 10 in a hollow cylindrical mold 20, as shown in FIG. 2a; pouring a first paste comprising a calcium phosphate cement and a setting liquid in the annular cell and a second paste comprising the calcium phosphate cement, a pore-forming powder and the setting liquid in the central cell, as shown in FIG. 2b; removing the partition wall and pressing the CPC pastes before hardening, as shown in FIG. 2c, wherein a portion of the setting liquid is removed from the gap between the mold 20 and the press 30 and/or holes (not shown in the drawing) provided on the press 30. The CPC paste will undergo a hardening reaction to convert into apatitic phase. The hardened disk is removed from the mold and is subjected to surface finishing to expose the central portion hardened from the second paste, as shown in FIG. 2d, followed by immersing in a bath of an immersing liquid as shown in FIG. 2e, where the pore-forming powder is dissolved in the immersing liquid while the hardened CPC thereof gaining compressive strength. The immersing may last from 10 minutes to several days. The composite disk so formed is washed with water after being removed from the bath, and dried and heated in an oven to obtain the prosthetic bone implant as shown in FIG. 2f. The heating is conducted at a temperature between 50 and 500° C. for a period of several hours to several days, which enhance the compressive strength of the cortical portion of the prosthetic bone implant.

Figure 3A:
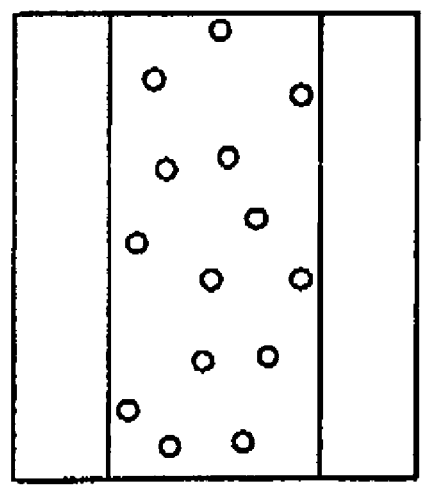
FIGS. 3a and 3b are schematic vertical and horizontal cross sectional views of a prosthetic bone implant prepared according to another embodiment of the present invention, respectively.
Figure 3B:
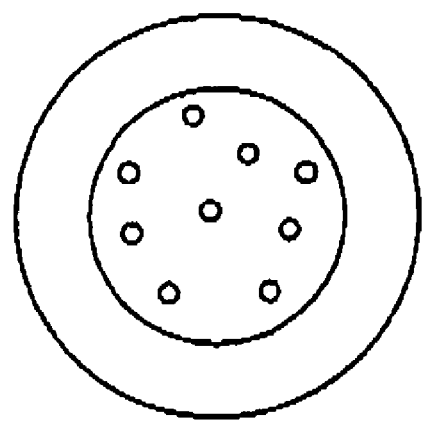

An alternative method for preparing the prosthetic bone implant of the present invention from the same raw materials includes pouring the second paste in a first mold, pressing the second paste to remove a portion of the setting liquid from the second paste before the hardening reaction is completed, so that the liquid/powder ratio in the second paste decreases, and allowing the hardening reaction undergo in the mold for a period of time, e.g. 15 minutes starting from the mixing of the CPC powder, the pore-forming powder and the setting liquid, to obtain a cylindrical block having a diameter of 7 mm. Then, the cylindrical block is removed from the first mold, and placed in the center of a second mold having a diameter of 10 mm. The first paste is poured into the annular space in the second mold, and a press having a dimension corresponding to the annular shape is used to pressure the first paste to remove a portion of the setting liquid from the first paste before the hardening reaction is completed, so that the liquid/powder ratio in the first paste decreases. Again, the first paste will undergo a hardening reaction to convert into apatitic phase. The hardened cylinder having a diameter of 10 mm is removed from the second mold, followed by immersing in an immersing liquid, where the pore-forming powder contained in the second paste is dissolved in the immersing liquid while the hardened CPC thereof gaining compressive strength, to obtain the prosthetic bone implant of the present invention, as shown in FIGS. 3a and 3b. It is apparently to people skilled in the art that the prosthetic bone implant shown in FIGS. 3a and 3b can also be prepared by changing the sequence of the molding of the first paste and the second paste with modifications to the second mold used in this alternative method.

The following examples are intended to demonstrate the invention more fully without acting as a limitation upon its scope, since numerous modifications and variations will be apparent to those skilled in this art.

PREPARATIVE EXAMPLE 1

Preparation of TTCP Powder

A $Ca_4(PO_4)_2O$ (TTCP) powder was prepared by mixing $Ca_2P_2O_7$ powder with $CaCO_3$ powder uniformly in ethanol for 24 hours followed by heating to dry. The mixing ratio of $Ca_2P_2O_7$ powder to $CaCO_3$ powder was 1:1.27 (weight ratio) and the powder mixture was heated to 1400° C. to allow two powders to react to form TTCP.

PREPARATIVE EXAMPLE 2

Preparation of Conventional TTCP/DCPA-Based CPC Powder (Abbreviated as C-CPC)

The resulting TTCP powder from PREPARATIVE EXAMPLE 1 was sieved and blended with dried $CaHPO_4$ (DCPA) powder in a ball mill for 12 hours. The blending ratio of the TTCP powder to the DCPA powder was 1:1 (molar ratio) to obtain the conventional CPC powder. Particles of this C-CPC powder have no whisker on the surfaces thereof.

PREPARATIVE EXAMPLE 3

Preparation of Non-Dispersive TTCP/DCPA-Based CPC Powder (Abbreviated as ND-CPC)

The TTCP powder prepared according to the method of PREPARATIVE EXAMPLE 1 was sieved and blended with dried $CaHPO_4$ (DCPA) powder in a ball mill for 12 hours. The blending ratio of the TTCP powder to the DCPA powder was 1:1 (molar ratio). The resultant powder mixture was added to a 25 mM diluted solution of phosphate to obtain a powder/solution mixture having a concentration of 3 g powder mixture per 1 ml solution while stirring. The resulting powder/solution mixture was formed into pellets, and the pellets were heated in an oven at 50° C. for 10 minutes. The pellets were then uniformly ground in a mechanical mill for 20 minutes to obtain the non-dispersive TTCP/DCPA-based CPC powder (ND-CPC). The particles of this ND-CPC powder have whisker on the surfaces thereof.

Dense Blocks

EXAMPLE 1

Effect of Immersion Time on Compressive Strength of CPC Block

To a setting solution of 1M phosphoric acid solution (pH=5.89) the ND-CPC powder from PREPARATIVE EXAMPLE 3 was added in a liquid/powder ratio (L/P ratio) of 0.4, i.e. 4 ml liquid/10 g powder, while stirring. The resulting paste was filled into a cylindrical steel mold having a length of 12 mm and a diameter of 6 mm, and was compressed with a gradually increased pressure until a maximum pressure was reached. The maximum pressure was maintained for one minute, and then the compressed CPC block was removed from the mold. At the $15^{th}$ minute following the mixing of the liquid and powder, the compressed CPC block was immersed in a Hanks' solution for 1 day, 4 days, and 16 days. Each test group of the three different periods of immersion time has five specimens, the compressive strength of which was measured by using a AGS-500D mechanical tester (Shimadzu Co., Ltd., Kyoto, Japan) immediately following the removal thereof from the Hanks' solution without drying. The CPC paste in the mold was compressed with a maximum pressure of 166.6 MPa, and in the course of the compression the compression speeds were about 5 mm/min during 0~104.1 MPa; 3 mm/min during 104.1~138.8 MPa; 1 mm/min during 138.8~159.6 MPa: and 0.5 mm/min during 159.6~166.6 MPa. The measured wet specimen compressive strength is listed Table 1.

TABLE 1

| Immersion time (Day) | Compressive strength (MPa) | Standard deviation (MPa) |
|---|---|---|
| No immersion | 37.3* | 0.6 |
| 1 day | 149.2 | 12.9 |
| 4 days | 122.7 | 6.7 |
| 16 days | 116.4 | 7.7 |

*This value was measured before the compressed CPC blocks were immersed in the Hanks' solution, and it was substantially the same for the compressed CPC blocks not immersed in the Hanks' solution measured a few days after the preparation.

It can seen from Table 1 that the compressive strength of the compressed CPC blocks is increased remarkably after one-day immersion in comparison with the non-immersed block, and declines a little for a longer immersion time.

EXAMPLE 2

Effect of Whiskers on Compressive Strength of TTCP/DCPA-Based CPC Block

The procedures of EXAMPLE 1 were repeated by using the C-CPC powder prepared in PREPARATIVE EXAMPLE 2 and the ND-CPC powder prepared in PREPARATIVE EXAMPLE 3. The maximum pressure used to compress the CPC paste in the mold in this example was 156.2 MPa. The results for one-day immersion time are listed in Table 2.

TABLE 2

| CPC powder | Compressive strength (MPa) | Standard deviation (MPa) |
|---|---|---|
| C-CPC (no whisker) | 62.3 | 5.0 |
| ND-CPC (with whisker) | 138.0 | 8.2 |

It can be seen from Table 2 that the compressive strength, 62.3 MPa, of the immersed compressed CPC block prepared from the conventional CPC powder (no whisker) is about 1.7 times of that (37.3 MPa) of the non-immersed compressed CPC block in Table 1, and the compressive strength, 138.0 MPa, of the immersed compressed CPC block prepared from the non-dispersive CPC powder (with whisker) is about 3.7 times of that of the non-immersed compressed CPC block in Table 1.

EXAMPLE 3

Effect of Whiskers on Compressive Strength of TTCP-Based CPC Block $Ca_4(PO_4)_2O$ (TTCP) powder as synthesized in PREPARATIVE EXAMPLE 1 was sieved with a #325 mesh. The sieved powder has an average particle size of about 10 μm. To the TTCP powder HCl aqueous solution (pH=0.8) was added according to the ratio of 1 g TTCP/13 ml solution. The TTCP powder was immersed in the HCl aqueous solution for 12 hours, filtered rapidly and washed with deionized water, and filtered rapidly with a vacuum pump again. The resulting powder cake was dried in an oven at 50° C. The dried powder was divided into halves, ground for 20 minutes and 120 minutes separately, and combined to obtain the non-dispersive TTCP-based CPC powder, the particles of which have whisker on the surfaces thereof. A setting solution of diammonium hydrogen phosphate was prepared by dissolving 20 g of diammonium hydrogen phosphate, $(NH_4)_2HPO_4$, in 40 ml deionized water. The procedures in EXAMPLE 1 were used to obtain the wet specimen compressive strength for one-day immersion time, wherein the maximum pressure to compress the CPC paste in the mold was 156.2 MPa. The results are shown in Table 3.

TABLE 3

| CPC powder | Compressive strength (MPa) | Standard deviation (MPa) |
|---|---|---|
| TTCP (no whisker) | 79.6 | 8.8 |
| TTCP (with whisker) | 100 | 4.2 |

The trend same as the TTCP/DCPA-based CPC powder in Table 2 of EXAMPLE 2 can be observed in Table 3.

EXAMPLE 4

Effect of Molding Pressure on Compressive Strength of ND-CPC Block (in Low Pressure Regime: 0.09~3.5 MPa)

The procedures of EXAMPLE 1 were repeated except that the maximum pressure used to compress the CPC paste in the mold was changed from 166.6 MPa to the values listed in Table 4. The period of immersion was one day. The results are listed in Table 4.

TABLE 4

| Pressure for compressing the CPC paste in mold (MPa) | Compressive strength (MPa) | Standard deviation (MPa) |
|---|---|---|
| 0.09 | 12.3 | 2.0 |
| 0.35 | 16.0 | 2.3 |
| 0.7 | 20.7 | 2.5 |
| 1.4 | 26.4 | 1.4 |
| 3.5 | 35.2 | 3.7 |

The data in Table 4 indicate that the compressive strength of the CPC block increases as the pressure used to compress the CPC paste in the mold increases.

EXAMPLE 5

Effect of Reducing Liquid/Powder Ratio During Compression of the CPC Paste in the Mold on Compressive Strength of ND-CPC Block The procedures of EXAMPLE 1 were repeated except that the maximum pressure used to compress the CPC paste in the mold was changed from 166.6 MPa to the values listed in Table 5. The liquid leaked from the mold during compression was measured, and the liquid/powder ratio was re-calculated as shown in Table 5. The period of immersion was one day. The results are listed in Table 5.

TABLE 5

| Pressure for compressing the CPC paste in mold (MPa) | L/P ratio (after a portion of liquid removed) | Compressive strength (MPa) | Standard deviation (MPa) |
|---|---|---|---|
| 1.4 | 0.25 | 26.4 | 1.4 |
| 34.7 | 0.185 | 75.3 | 3.9 |
| 69.4 | 0.172 | 100.4 | 6.8 |
| 156.2 | 0.161 | 138.0 | 8.2 |
| 166.6 | 0.141 | 149.2 | 12.9 |

The data in Table 5 show that the compressive strength of the CPC block increases as the liquid/powder ratio decreases during molding.

EXAMPLE 6

Effect of Post-Heat Treatment on Compressive Strength of CPC Block

The procedures of EXAMPLE 1 were repeated. The period of immersion was one day. The CPC blocks after removing from the Hanks' solution were subjected to post-heat treatments: 1) 50° C. for one day; and 2) 400° C. for two hours with a heating rate of 10° C. per minute. The results are listed in Table 6.

TABLE 6

|  | Compressive strength (MPa) | Standard deviation (Mpa) |
|---|---|---|
| No post-heat treatment | 149.2 | 12.9 |
| 50° C., one day | 219.4 | 16.0 |
| 400° C., two hours | 256.7 | 16.2 |

It can be seen from Table 6 that the post-heat treatment enhances the compressive strength of the CPC block.

Porous Blocks

EXAMPLE 7

Effect of KCl Content and Immersion Time on Compressive Strength of Porous CPC Block To a setting solution of 1M phosphoric acid solution (pH=5.89) the ND-CPC powder from PREPARATIVE EXAMPLE 3 was added in a liquid/powder ratio (L/P ratio) of 0.4, i.e. 4 ml liquid/10 g powder, while stirring. KCl powder in a predetermined amount was mixed to the resulting mixture by stirring intensively. The resulting paste was filled into a cylindrical steel mold having a length of 12 mm and a diameter of 6 mm, and was compressed with a gradually increased pressure until a maximum pressure of 3.5 MPa was reached. The maximum pressure was maintained for one minute, and then the compressed CPC block was removed from the mold. At the 15$^{th}$ minute following the mixing of the liquid and powders, the compressed CPC block was immersed in a deionized water at 37° C. for 4 days, 8 days, and 16 days. The compressive strength of the specimens of the three different periods of immersion time was measured by using a AGS-500D mechanical tester (Shimadzu Co., Ltd., Kyoto, Japan) after the specimens were dry. The measured dry specimen compressive strength is listed Table 7.

TABLE 7

| KCl/CPC ratio by weight | Dry compressive strength (MPa) Immersion time (Day) | | |
|---|---|---|---|
| | 4 days | 8 days | 16 days |
| 1 | 7.0 | 5.4 | 6.6 |
| 1.5 | 3.9 | 2.7 | 4.3 |
| 2 | 1.3 | 2.3 | 2.6 |

It can seen from Table 7 that the dry compressive strength of the porous CPC blocks decreases as the KCl/CPC ratio by weight increases.

EXAMPLE 8

Porosity and Compressive Strength of Porous CPC Blocks Prepared from Different Pore-Forming Powders The procedures of EXAMPLE 7 were repeated by using sugar, KI, $C_{17}H_{33}COONa$ and $C_{13}H_{27}COOH$ instead of KCl. The immersion time was 14 days in deionized water. In the cases where the $C_{17}H_{33}COONa$ and $C_{13}H_{27}COOH$ were used, the CPC blocks were further immersed in ethanol for additional four days. The conditions and the results are listed in Table 8.

TABLE 8

| Pore-forming powder | S[a] | C.S. (MPa)[b] | Porosity (vol %)[c] |
|---|---|---|---|
| Sugar | 1 | 4.1 | 58.4 |
| KI | 2 | 4.3 | 62.2 |
| KI | 3 | 1.7 | 75.5 |
| C17H33COONa | 1 | 8.0 | 56.0 |
| C13H27COOH | 2 | 5.9 | 60.1 |

[a] S = Pore-forming powder/CPC by volume.
[b] C.S. = dry compressive strength (hereinafter abbreviated as C.S.).
[c] Porosity: Porosity (vol %) was measured by Archimedes' method, and calculated as in ASTM C830.

It can be seen from Table 8 that various powders which are soluble in water can be used in the preparation of a porous CPC block according to the method of the present invention.

Dual-Functional Block

EXAMPLE 9

To a setting solution of 1M phosphoric acid solution (pH=5.89) the ND-CPC powder from PREPARATIVE EXAMPLE 3 was added in a liquid/powder ratio (L/P ratio) of 0.4, i.e. 4 ml liquid/10 g powder, while stirring. KCl powder in a ratio of KCl powder/CPC by volume of 2 was mixed to the resulting mixture by stirring intensively. The resulting paste was filled into a cylindrical steel mold having a length of 12 mm and a diameter of 7 mm, and was compressed with a gradually increased pressure until a maximum pressure of 3.5 MPa was reached. The maximum pressure was maintained for one minute, and then the compressed CPC block was removed from the mold at the 15$^{th}$ minute following the mixing of the liquid and powders.

The resulting cylinder having a diameter of 7 mm was placed in another cylindrical steel mold having a diameter of 10 mm. To a setting solution of 1M phosphoric acid solution (pH=5.89) the ND-CPC powder from PREPARATIVE EXAMPLE 3 was added in a liquid/powder ratio (L/P ratio) of 0.4, i.e. 4 ml liquid/10 g powder, while stirring. The resulting paste was filled into the gap between said cylinder and said another mold, and was compressed with a gradually increased pressure until a maximum pressure of 50 MPa was reached. The maximum pressure was maintained for one minute. At the 15$^{th}$ minute following the mixing of the liquid and ND-CPC powder, the CPC/KCl composite block was immersed in a deionized water at 37° C. for 4 days. KCl powder was dissolved in the deionized water, and a dual-functional CPC block having a porous CPC cylinder surround by a dense CPC annular block was obtained.

The compressive strength of the specimen was measured by using a AGS-500D mechanical tester (Shimadzu Co., Ltd., Kyoto, Japan) after the specimens were dry. The measured dry specimen compressive strength is 68.8 MPa.

The porosities of the porous CPC cylinder and the dense CPC annular block were measured by Archimedes' method, and calculated as in ASTM C830, after the dual-functional CPC block was broken intentionally, and the results are 74% and 30%, respectively.

X-ray diffraction pattern of the powder obtained by grinding the dual-functional CPC block shows broadened characteristic X-ray diffraction peaks of apatite at $2\theta=25-27°$ and $2\theta=20-35°$ with a scanning range of $2\theta$ of 20–40° and a scanning rate of 1° results indicate that the powder is a mixture of apatite and TTCP with apatite as a major portion.

What is claimed is:

1. A method for increasing the compressive strength of a prosthetic bone implant comprising:
    forming a prosthetic bone implant, the prosthetic bone implant comprising one or more porous components coupled to at least one load bearing component; and
    subjecting the prosthetic bone implant to one or more heat treatments, wherein the temperature of the heat treatments is from about 50° C. to about 500° C.

2. The method of claim 1, wherein the maximum temperature of the heat treatment is achieved over a predetermined amount of time.

3. The method of claim 2, wherein subjecting the prosthetic implant to one or more heat treatments comprises heating the prosthetic bone implant from a first temperature to a second temperature, wherein the second temperature is greater than the first temperature, and wherein the rate of temperature increase that the prosthetic bone implant is subjected to is about 10° C. per minute.

4. The method of claim 1, wherein the heat treatment is carried out for at least two hours.

5. The method of claim 1, wherein the heat treatment is carried out for at least one day.

6. The method of claim 1, wherein the heat treatment substantially dries the prosthetic bone implant.

7. The method of claim 1, further comprising immersing the prosthetic bone implant in one or more immersing liquids for a predetermined period of time.

8. The method of claim 7, wherein immersing the prosthetic bone implant increases the compressive strength of the prosthetic bone implant.

9. The method of claim 7, wherein the prosthetic bone implant is immersed in at least one immersing liquid for at least 10 minutes.

10. The method of claim 7, wherein the prosthetic bone implant is immersed in at least one immersing liquid for at least 24 hours.

11. The method of claim 7, wherein immersion of the prosthetic bone implant is carried out at a temperature of from about 10° C. to about 90° C.

12. The method of claim 7, wherein at least one immersing liquid comprises at least one source of calcium and at least one source of phosphate.

13. The method of claim 7, wherein at least one immersing liquid comprises Hank's solution.

14. The method of claim 7, wherein at least one immersing liquid comprises substantially pure water.

* * * * *